United States Patent [19]

Tanner et al.

[11] Patent Number: 5,624,681
[45] Date of Patent: Apr. 29, 1997

[54] TAMPER EVIDENT PHARMACEUTICAL DOSAGE FORM

[75] Inventors: Keith Tanner, Safety Harbor; Kelly Orange, St. Petersburg, both of Fla.

[73] Assignee: R. P. Scherer Corporation, Troy, Mich.

[21] Appl. No.: 427,895

[22] Filed: Apr. 26, 1995

[51] Int. Cl.$^6$ ..................................... A61K 9/48
[52] U.S. Cl. .................. 424/454; 424/456; 424/458; 424/489; 424/490; 424/492
[58] Field of Search .................. 424/454, 455, 424/456, 453, 452, 465, 458, 489, 490, 492

[56] References Cited

U.S. PATENT DOCUMENTS

| | | | |
|---|---|---|---|
| 4,844,906 | 7/1989 | Hermelin et al. | 424/454 |
| 5,089,270 | 2/1992 | Hampton et al. | 424/465 |

FOREIGN PATENT DOCUMENTS

WO9501787  1/1995  WIPO.

OTHER PUBLICATIONS

Cooper et al., *Liquid and Solid Solution Interactions of Primary Certified Colorants With* Pharmaceutical Gelatins, Journal of Pharmaceutical Sciences, pp. 1156–1164.

*Primary Examiner*—Thurman K. Page
*Assistant Examiner*—Sharon Howard
*Attorney, Agent, or Firm*—McDonnell Boehnen Hulbert & Berghoff

[57] ABSTRACT

A dosage form for pharmaceuticals, nutrient supplements and food products which is nontoxic and suitable for introduction into mammalian bodies comprising soft elastic gelatin capsule containing a colorless clear liquid carrier and an active ingredient. The capsule is rendered particularly tamper evident by color neutralizing its inherent amber/yellow color with edible dyes and pigments.

15 Claims, No Drawings

TAMPER EVIDENT PHARMACEUTICAL DOSAGE FORM

BACKGROUND OF THE INVENTION

Field of the Invention and Description of the Prior Art

This invention is concerned with dosage forms containing an active ingredient for human ingestion. More specifically, it is concerned with edible dosage unit forms which comprise soft elastic gelatin (SEG) capsule shells encapsulating an active ingredient.

Pharmaceutical compositions in dosage unit form encapsulated in SEG capsules are well known and generally consist of a fill material comprising one or more active ingredients dissolved or suspended in an appropriate liquid or paste vehicle encapsulated in a soft gelatin shell, typically comprising gelatin together with a plasticizer. Standard gelatin used to manufacture soft elastic gelatin capsules has a yellow coloration inherent from the manufacturing process. Thus, when an SEG capsule is produced with a colorless transparent fill material and a standard gelatin, capsules appear visually as a clear amber to yellow color. The interior liquid in the capsule can be a single or a multi-component system; in either case it must be chemically compatible with the SEG capsule.

Particularly in recent years, ingredient adulteration of ingestible dosage forms, especially pharmaceuticals, has come to public attention as a risk inherent in ingesting over-the-counter and prescription drugs. Manufacturers' approaches to deal with this problem have generally involved some form of seal on the medication's package, so that the seal will give evidence of having been broken if the product has been tampered with. Examples of such seals include shrink wrapping the entire container, placing a tab seal across the junction between the cap or top and the side of the container, and enclosing the neck of a bottle at the cap/bottle interface in a continuous loop of tightly applied plastic film. Some containers have also been designed with a pop up indicator that moves from a position flush with the rest of the package to a raised position to indicate when the package has been opened.

At the dosage form level, one alternative is two piece hardshell capsules which are sealed with a shrunken band to prevent separation of the two pieces.

In the separate field of cosmetics, packages are less strictly monitored for adulteration than pharmaceutical dosage form packages because the former products are not intended for ingestion. A wide variety of packaging is used in cosmetics, such as compacts, atomizers, boxes, slide tubes, tins, colored pencils, and jars. At least one cosmetic product, Elizabeth Arden's UNDER EYE CERAMIDE MOISTURIZER product has been sold in a soft gel capsule which acts exclusively as the packaging and applicator. Color neutralization techniques have been used for making this soft gel packaging, employing dyes, such as D&C Violet #5, for aesthetic purposes.

SUMMARY OF THE INVENTION

Prior art methodology to render pharmaceuticals tamper evident was focused primarily on the exterior packaging for the drug dosage form. The present invention offers a unique and alternative approach to rendering soft gel pharmaceutical dosage forms more tamper evident. In particular, applicants have invented a tamper evident dosage form suitable for human ingestion comprising a transparent color-neutralized nontoxic soft elastic gelatin capsule containing a colorless, clear liquid carrier and an active ingredient. The carrier and active ingredient may be different, or may be one and the same.

Currently, soft gel capsules for internal administration are produced containing no dye or pigment additives to the gelatin shell. The result is a transparent capsule with a residual amber coloration. The intensity of the amber color can be attenuated by carefully selecting gelatin grades with a low base color. However, crystal clear colorless capsules are not achievable by this method. Presently, careful physical examination of a capsule is necessary to see if the capsule wall has been punctured and resealed such that the capsule has been adulterated. If the adulteration has been performed skillfully, it may be difficult for the untrained eye to observe.

In contrast, the present invention provides a clear, color neutralized soft gel with improved tamper evidence. The tamper evidence is improved in at least two respects. First, it permits simpler identification of altered dosage unit forms since the introduction of adulterants that have a base color or cause some sort of physical change within a capsule affect the appearance of the capsule providing a visual check of tampering. Secondly, it is focused on the dosage form level rather than on the packaging level, so that adulteration of individual capsules before their packaging would also be evident.

Color neutralization of the soft gels is accomplished by combining the primary colors red, yellow and blue with matched intensities to neutralize the component colors of the gelatin, producing a neutral colorless shade. This is achieved through the addition of small amounts of edible dyes and pigments to the gelatin mass used to produce a gelatin shell. In a preferred embodiment of the invention, the fill material is a colorless, clear liquid.

It is an advantage of the invention that it defines a method for producing an edible soft gel capsule that has essentially no base color. It is another advantage of the invention that the clear, colorless dosage form for drugs and other active ingredients will have great tamper evidence; that is, in the instance of a capsule that has been adulterated or tampered with, it is more likely that alteration to the color or overall appearance of the capsule will be noticeable.

It is a further advantage of the invention that quality control examination of capsules will be simplified by the inventive transparent color-neutralized soft elastic gelatin capsule dosage forms containing a clear, colorless carrier and active ingredient(s).

An additional advantage of the invention is that it provides an aesthetically pleasing novel appearance to a drug dosage form. The visual appearance of capsules produced according to the invention is significantly different from conventional capsules. This difference may be used to differentiate products on an aesthetic basis. The clarity and lack of color of the dosage form may also connote certain attributes of the product such as purity and/or effectiveness.

Thus, the invention contemplates a tamper evident dosage form suitable for introduction into the human body comprising a transparent color-neutralized soft elastic gelatin capsule containing a colorless, clear liquid carrier and an active ingredient.

DESCRIPTION OF THE PREFERRED EMBODIMENTS

This invention provides a new type of dosage form suitable for ingestion or other introduction into the mammals body. Administration of the dosage form may be oral, rectal or by vaginal insertion. Most commonly, the administration will be by the oral route.

The soft elastic gelatin capsule is formulated for use in the invention by special techniques to render the dosage form tamper evident and to give it novel aesthetics. The additives employed to achieve this goal must be nontoxic and approved for human use. By the addition of edible dyes and pigments to the gelatin mass used to produce the gelatin shell, neutralization of the base yellow color can be achieved. The effect of neutralizing the yellow color is to produce a capsule that appears visually to have no color, i.e., colorless. The overall dosage form appears colorless when produced with a colorless, clear filler. To achieve the color neutralization effect extremely small additions of dyes and pigments are required to be added to the gelatin. Colors used are combinations of red, green and/or blue that will combine with the residual yellow color to produce a virtually colorless shade.

Gelatin is supplied commercially as a granule, and for the purpose of this invention, it is desirable, but not essential, that a grade be used that has a low initial base color. Typically the gelatin is animal derived; examples include high bloom bovine bone or hide or pig hide extractions. The color neutralized gelatin mass is prepared by the following method.

Granular gelatin is heated with suitable proportions of water and plasticizers, such as glycerin and/or sorbitol. The mass becomes molten at temperatures above 55 to 60 degrees centigrade. To the molten mass, small quantities of dyes and/or pigments are added, sufficient to neutralize the yellow base color. These are dissolved/dispersed uniformly into the gelatin mass using a high speed blender. The molten mass is cast into ribbons, and the capsules are produced from the ribbons using standard rotary die encapsulation machinery.

The dyes and/or pigments employed in the invention must be nontoxic in the levels used. Examples of U.S. FDA approved dyes and pigments that can be used in various combinations to achieve the color neutralized effect are listed below:

DYES
FD&C BLUE #1
FD&C BLUE #2
FD&C GREEN #5
FD&C GREEN #3
FD&C RED #40
D&C RED #33
PIGMENTS
All corresponding inorganic lakes of the dyes listed above
Carmine red
Iron sequestoxides (all color forms)

Additional dyes or pigments that can be used in various combinations to achieve the color neutralization effect include Erythrosine, Ponceau 4R, Red 2G, Amaranth, Patent Blue V and Green S.

A gelatin capsule shell in a swallowable product is an integral component of the dosage form and cannot be described as packaging. In contrast, the prior art Elizabeth Arden UNDER EYE CERAMIDE MOISTURIZER product is an external use only product where the capsule functions as the primary packaging, not as the dosage form, and where it incorporates inedible dyes such as D&C Violet #5, which is restricted by U.S. legislation to external use only.

Preferably, the fill material for the SEG capsules is a colorless clear liquid. The drug solutions or other filler liquids within the capsule are preferably clear and completely colorless. Alternatively, the capsule may contain microbeads or suspended particles in a colorless clear carrier liquid. The active agent in the filler may be a prescription or over the counter drug, a nutritional supplement, veterinary products or a food product. The active ingredient and the carrier liquid may be different, or may be one and the same.

Examples of color neutralized gelatin masses follow.

EXAMPLE 1

| Component | Amount Kilograms |
| --- | --- |
| Gelatin Mass (Gelatin) Glycerin, Sorbitol, Water | 100.0 |
| FD&C Green # 5 | 0.0020 |
| D&C Red # 33 | 0.0018 |
| FD&C Blue # 1 | 0.0024 |

EXAMPLE 2

| Component | Amount Kilograms |
| --- | --- |
| Gelatin Mass (Gelatin, Glycerin, Sorbitol, Water) | 100.0 |
| FD&C Green # 5 | 0.0059 |
| D&C Red # 33 | 0.0020 |

A typical formulation of a colorless clear liquid fill material which may be employed with a color neutralized soft elastic gelatin capsule is provided below.

EXAMPLE 3

| Component | % Composition of Fill w/w |
| --- | --- |
| Acetaminophen | 27.2 |
| PEG 400 | 54.8 |
| Propylene Glycol | 5.0 |
| Polyvinyl Pyrrolidone | 5.0 |
| Water | 8.0 |

Depending upon the nature of the gel capsule being color neutralized, the relative amounts of the various color components can be as much as five times more or less than the specific amounts stated above.

In another embodiment of the invention, the fill material for the SEG capsules is also separately color neutralized. As with the capsule shell, this may be accomplished by adding appropriate amounts of neutralizing base colors to the fill of the capsule. The total visual effect of having a color neutralized fill material inside a color neutralized SEG capsule shell is the same, a substantially window clear capsule. However, if any portion of the fill is removed, and an adulterant is added to the capsule, the delicate balance of colors will be disturbed as a result of a dilution effect. The fill material will no longer be clear, and will instead exhibit a color, such as amber. Because the color combination of the liquid would be unknown to a person attempting to adulterate the dosage form, it would be extremely difficult to achieve the correct delicate color balance in the adulterant to recreate the window clear effect, thus providing evidence of tampering.

In still another embodiment of the invention, the added color components necessary to achieve the window clear effect could be distributed between the shell to give the first color and the fill to give the second color on a partial or complete basis. For example, blue could be added to the fill in appropriate amounts, with green and red being incorporated into the capsule in appropriate amounts, to provide an overall color neutralized dosage form. While both the capsule and the fill would be independently colored, the dosage form would be color neutralized on an overall basis once the gel and the liquid are combined. Alternatively, each color could be distributed equally between the fill and the shell, to provide an overall color neutralized dosage form. Again, addition of an adulterant would upset the color balance, revealing tampering. It will be understood to persons of ordinary skill in the art that the specific amount of base colors to be added to the capsule or to the fill liquid or to both will vary from case to case, depending on the nature and color of the capsule and fill liquid being used. In general, the specific amount of each base color is best determined by titrating the various components with the base colors, until the desired color or colorless result is achieved.

It should be understood that the foregoing disclosure emphasizes certain specific embodiments of the invention and that all modifications and alternatives equivalent thereto are within the spirit and scope of the invention as set forth in the appended claims.

We claim:

1. A tamper evident dosage form suitable for introduction into a mammalian body, consisting of a transparent color-neutralized nontoxic soft elastic gelatin capsule containing a colorless, clear liquid carrier and an active ingredient selected from the group consisting of a pharmaceutical, a nutritional supplement and a food product.

2. The dosage form of claim 1 wherein the transparent color-neutralized nontoxic soft elastic gelatin capsule is comprised of animal-derived gelatin, water, plasticizer and edible dyes and pigments present in amounts and proportions which essentially neutralize the inherent color of the gelatin.

3. The dosage form of claim 2 wherein the gelatin has a low initial base color.

4. The dosage form of claim 3 wherein the gelatin is selected from the group consisting of high bloom bovine bone or hide and pig hide extractions.

5. The dosage form of claim 3 wherein the color neutralizing dyes and pigments are selected from the group consisting of FD&C Blue #1, FD&C Blue #2, FD&C Green #5, FD&C Green #3, FD&C Red #40, D&C Red #33, the corresponding inorganic lakes of the former, carmine red, and all color forms of iron sequestoxides.

6. The dosage form of claim 1 wherein the carrier liquid and active ingredient are different.

7. The dosage form of claim 1 wherein the carrier liquid and active ingredient are one and the same.

8. The dosage form of claim 1 wherein the active ingredient is in solution in the carrier liquid.

9. The dosage form of claim 1 wherein the active ingredient is in the form of microbeads or suspended particles in a colorless clear carrier liquid.

10. The dosage form of claim 1 wherein the active ingredient is a pharmaceutical.

11. The dosage form of claim 1 wherein the active ingredient is a nutritional supplement or food product.

12. The dosage form of claim 1 wherein the liquid carrier is color neutralized.

13. The dosage form of claim 12 wherein the active ingredient is in the form of microbeads or suspended particles.

14. A tamper evidence dosage form suitable for introduction into a mammalian body, consisting of a nontoxic soft elastic gelatin capsule containing a liquid carrier and an active ingredient, the gelatin capsule having a first color and the liquid carrier having a second color that substantially neutralizes the first color, whereby the dosage form is substantially clear and colorless.

15. The dosage form of claim 14 wherein the active ingredient is in the form of microbeads or suspended particles.

* * * * *